United States Patent [19]

Otten

[11] Patent Number: 5,667,796
[45] Date of Patent: Sep. 16, 1997

US005667796A

[54] METHOD FOR PRODUCING CERAMIC IMPLANT MATERIALS, PREFERABLY CERAMIC IMPLANT MATERIALS INCLUDING HYDROXYL APATITE

[76] Inventor: Klaus Otten, Im Pfarrgarten 4a, D-64404 Bickenbach, Germany

[21] Appl. No.: 658,526

[22] Filed: Jun. 5, 1996

Related U.S. Application Data

[63] Continuation of Ser. No. 346,464, Nov. 29, 1994, abandoned.

[30] Foreign Application Priority Data

Nov. 30, 1993 [SE] Sweden .................................. 9303977

[51] Int. Cl.⁶ .................................................. A61F 13/00
[52] U.S. Cl. .......................... 424/422; 424/423; 424/426
[58] Field of Search ..................................... 424/422, 423, 424/426; 523/115; 530/353, 354, 355, 356; 623/18

[56] References Cited

U.S. PATENT DOCUMENTS 4,654,464   3/1987   Mittelmeier et al. .................... 623/16
5,306,302   4/1994   Bauer et al. .............................. 623/16

*Primary Examiner*—Thurman K. Page
*Assistant Examiner*—Sharon Howard
*Attorney, Agent, or Firm*—Tarolli, Sundheim, Covell, Tummino & Szabo

[57] ABSTRACT

The present invention relates to a method for production of ceramic implant material, preferably ceramic implant material including hydroxyl apatite. According to the invention, for the production, the spongy parts of joints from animals, preferably grown-up cattle, are used, whereby the organic constituents of the spongy parts of the joints are removed by a quick burning, whereby one or more flushings of the remaining inorganic parts of the joints are effected without chemical additives and whereby said inorganic parts of the joints are sintered. The implant material can be used in connection with a mark inoculation method and in cell cultures.

25 Claims, No Drawings

METHOD FOR PRODUCING CERAMIC IMPLANT MATERIALS, PREFERABLY CERAMIC IMPLANT MATERIALS INCLUDING HYDROXYL APATITE

This is a continuation of application(s) Ser. No. 08/346,464 filed on Nov. 29, 1994 now abandoned.

The use of implant materials including hydroxyl apatite during medical treatment of patients having defects in or on the skeleton, has after initially careful tests been shown to be effective. The medical drawbacks occuring at the time when implants of ceramic materials of calcium phosphate were first used, have now been identified. The reason hereto was primarily the artificial and complex production methods, particularly the use of more compact ceramic materials, and the ignorance of the real crystalline composition as well as the for the most part unsuitable sintering temperatures.

These disadvantageous effects of ceramic materials including calcium phosphate were effectively counteracted through the development of biological bone replacement materials based on hydroxyl apatite. The introduction of ceramic bone replacement materials produced from biological basic materials such as algae, corals and bones has here been of great importance to the acceptance of these ceramic materials. Especially the development of the so called ceramic bone materials with their excellent Conformity regarding structure and composition, has increased the interest for bone replacement materials based on ceramic materials of hydroxyl apatite medically as well as economically.

Thus, the development concerning ceramic materials of hydroxyl apatite and bovine origin has brought about a number of technological advancements which today in patent specifications and products on the market are regarded as the present state of the technique.

Principally, one starts from bovine materials, i.e. materials from cattle, which through various methods are first relieved from albuminoids or proteins and thereafter heat sintered. The origin of this development is found in the material described in DE-C-961 654, which material is known as the "Kieler Knochenspan" but which for drug legal reasons no longer may be used. According to the method described in EP-A-0 141 004, the bone is first relieved from its soft parts, whereafter the albuminoids are removed chemically (10% solution of $H_2O_2$) and, in connection therewith, a sintering. Something similar is described in U.S. Pat. No. 4,314,380, whereby here, except for $H_2O_2$, NaOH is also used while however, the sintering temperatures are not reached. The method defined in DE-C-37 27 606 starts from a lenient pyrolytic removal of organic constituents, whereby, after a lenient drying, a pyrolysis occurs at a deficit of air or in a reducing atmosphere with subsequent oxidative sintering. According to the method published in DE-A-40 28 683, the stability problems at the method of DE-C-37 27 606 are eliminated by treatment with organic acids between pyrolysis and sintering.

Common to all said methods is the lenient removal of organic constituents either by chemical remedies or a reducing atmosphere and additionally, in an intermediate step in said last-mentioned method, treatment with acid. Common is also the subsequent sintering.

The major drawbacks with all these methods are the use of chemical additives for the production as well as the energetically and, as regards time consumption, extensive lenient removal of organic constituents in the pyrolysis.

The object of the present invention is in a first step to avoid all use of chemical substances during production, substantially improve the energy demanding part of the lenient pyrolysis, also in view of considerations regarding environmental protection, and permit variation of the crystal sizes and regulation of basicity and porosity.

According to the invention this is arrived at while for the production of the new ceramic bone material according to the invention, the porous or spongy parts of the joint balls of animals, preferably grown-up cattle, are subjected to a very quick temperature process with multiple excess of air without damaging the structure of the spongy beams. In connection therewith, storing is carried out respectively a permanent or intermittent treatment with water is effected for a natural reduction of excess of calcium and/or after a classic sintering further storing or enveloping in water mist is carried through.

Regarding the porosity, the use of animals, preferably grown-up cattle, has been shown to be particularly suitable for extracting the spongy parts of leg and arm joints, since the trabekel-structure is fully developed and large portions with the same pore structure are present. The shrinkage in three dimensions caused by the ceramic sintering results in that during use of said joint portions, the oversized pore-size distribution descending from cattle is reduced to the pore-size distribution for the corresponding human porous or spongy parts.

Surprisingly it has been noticed that not pretreated bone can be subjected to a quick temperature effect without damaging the structure thereof and the crematorium effect of disintegrating bone can be prevented or stopped. According to the invention, the removal of organic constituents is accelerated by quickly inserting a cold or frozen bone piece into a hot furnace and keeping it therein for a short time with increased air exchange. Hereby, the organic constituents are burnt from the outside and inwards so that when the outside is free from these constituents, the inside is still frozen. Thereby, one can effectively prevent melting or coking fat or other tissue from obstructing the pores and that thereby a detrimental overpressure is generated in the interior of the part. This process lasts for a few minutes and covers at the same time the major part of the energy demand for the process, since the burning of the organic constituents proceeds strongly exotherm, whereby the time saved according to the invention during removal of the organic constituents is attained and additionally, the energy consumption according to the invention is drastically reduced. Regarding the active environmental protection, the use of air in excess in connection with the generated burning or combustion gases is suitable for maintaining a catalytic after-burning of exhaust gases which in turn, along with heat from said after-burning further contribute to preheating of the burning or combustion air. Another effect attained according to the invention during this quick burning is that the crystals in the inorganic matrix of the inserted bone is only insignificantly altered in their initial size, since the crystals have no/little time to grow. Thereby, it is achieved that in order to later obtain the required crystallite size, one can on the whole start from the original crystallite size so that the least crystallite size in the later finished product is only somewhat above the original crystallite size. This production step permits removal of the organic matrix and stabilization of the inorganic constituents, whereby one here do not talk about a sintering effect but about a procees in the ceramic material designated as burning (stabilization of a matrix without the occurence of sintering features). By the optional subsequent storing or overspraying with fresh water, the inorganic constituents not adhering to the skeleton are washed away while at the same time easily dissolvable components are reduced and homogenized. Thereafter, the classic ceramic sintering is carried through, whereby the required time periods and temperatures can be adapted to the desired crystallite size, as can the bond resistance and degree of sintering be adjusted by the selection of appropriate time and temperature. Optional to the first storing or overspraying with water mist, further bathing in or overspraying with water may be carried out. By this concluding flushing, the amount of constituents present on the surface and affecting the basicity in a medium is successively reduced. The effect of this water treatment after sintering is that it will be possible to set or adjust the basicity of the ceramic implant material from e.g. pH 6.0 to pH 13.0, which after a further temperature treatment can be stabilized. Forming and compacting of the implant material thus obtained can be carried out in any known manner corresponding to the present state of the technique.

The production of a ceramic implant of hydroxyl apatite is described below with examples of the parameters used when carrying out the present method.

Epiphysary spongiosa (porous or spongy tissue) is extracted from the hip joint of grown-up cattle by sawing said joint in 2.7×2.7 cm large strips in any suitable length. The epiphyse strips are frozen to −18° C. within a time period of ten hours. The frozen epiphyse strips are placed on a fireproof sleigh or slide and quickly inserted into a furnace preheated by hot air—chamber temperature at insertion 650° C.—with a permanent excess of air oxygen of more than 2. The insertion step takes two seconds. The epiphyse bone being transformed is kept in this atmosphere for exactly ten minutes, whereby the newly added hot air flows directly to and through respectively, the epiphyse bone. The waste heat and exhaust gases generated through direct burning or combustion are subject to catalytic exhaust after-burning, whereafter the waste heat therefrom is used for heating newly added air. After ten minutes the epiphyse bone is removed from the furnace and cooled. The inorganic part of the epiphyse bone, now relieved from fat and other tissue and wherein at the most remains of carbon is present, has such a sufficient strength that it without problems can be oversprayed with water for 1.5 hours. The waste water may thereby be recovered and recirculated to the process. The burnt and washed epiphyse bone is now heated in atmospheric air with up to 2 Kelvin per minute to a final temperature of 1250° C., which is maintained for 90 minutes. After cooling, the newly sintered ceramic epiphyse bone material is once again oversprayed with water for six hours. The waste water can also here be recirculated and used again after recovery. Hereafter, a forming step is carried out by cutting off the end pieces of the ceramic epiphyse strips so that a part having a size of 2×2×5 cms is obtained. The implant obtained has the quality required according to ASTM for ceramic materials of hydroxyl apatite for use as implant materials. Just before compacting, the ceramic epiphyse implant is once again quickly heated to 900° C. and packed in a sterile atmosphere in sterile glass containers. If no sterile filling is possible, the parts are finally subjected to jet, gas or thermal sterilization.

The variations in the production of ceramic implant materials according to this method start already when selecting the bone. Suitable for the production in question are the epiphyse and metaphyse parts in the joint inner portions of hip joint, knee joint, shoulder joint and elbow joint on grown-up cattle, preferably epiphyse spongiosa from the hip joint. During preparation of the bone for the high-speed burning, the temperature may vary between elevated room temperature and down to −80° C. The best result is obtained at a temperature of about −15° C. In the high-speed burning or combustion chamber, the temperature can lie just above the ignition or inflammation temperature of the bone and may maximally increase to the phase transformation temperature of hydroxyl apatite. Tests with temperatures between 650° and 900° C. gave here good energetic results. The air exchange factor is depending on the plant used and must at least permit burning without residuals of the organic constituents and after-burning without problem of the exhaust gases. A tenfold air exchange has been shown to be suitable for the test apparatus. This can be adjusted individually based on the type and size of the furnace. The dwell time of the parts in the high-speed burning or combustion chamber is adapted to the size of said parts and the number of air exchanges in connection with the dimensions of the furnace plant, and can extend from a few seconds to several minutes. In the test plant with a raw bone measure of 2.7 cms and a temperature of 650° C. with tenfold air exchange, ten minutes was considered optimal. The exhaust gas afterburning can occur catalytically or thermally, whereby the recovery of waste heat may occur as in prior art. Fresh water shall be used for the first wash, i.e. water without minerals and organic compounds, whereby the use of demineralized water is considered sufficient. The first flushing may, when it is effected, last from a few seconds to several days. In the present example, an overspraying time of five hours has been suitable for the desired result. The object with a crystallization growth with a factor 100 was reached with a sintering temperature of 1250° C. and a dwell time of three hours. The variation possibilities lie at a sintering temperature of from 1100° C. up to phase transformation temperature, and a dwell time of from no dwell time at all to several days, whereby the form of ceramic bond and the crystallite size can be adjusted. The subsequent second flushing with water may last from a few seconds to several days. For the desired object, an overspraying time with watermist for six hours has been shown to be optimal. If the last wash is carried out with sterile water, the temperature treatment following the drying is no longer necessary. However, if pyrogen freedom is appreciated, the implant material is thereafter treated thermally with a minimum temperature of 300° C. or a maximum temperature at which crystallites start to change.

Instead of the washing treatment, it is possible by means of dotted noble metal solutions also to permit an integration of metals in the ceramic matrix, which at least as regards silver can give an effective protection against infections. Moreover, the finished ceramic implant may be provided with active substances of any suitable kind in any prior art manner. Thus, a combined preparation of e.g. a material of ceramic hydroxyl apatite as referred to above and provided with antibiotics can be obtained as final products, or addition can be effected of growth promoting preparations or is a so called mark inoculation carried out or simply an impregnation with blood. All methods can also be used in combination.

The method according to the invention can be used for the production also of other ceramic implant materials than such materials including hydroxyl apatite. During production of the ceramic implant material it is also possible to use the spongy parts of the joints from other animals than grown-up cattle.

The method defined can also be used for all other animals, whereby the composition of the obtained ceramic material can exhibit corresponding deviations from the ideal composition of the hydroxyl apatite.

An implant material thus produced can be used particularly for cultivating in vitro of cartilage and bone tissue or as a base substance for diagnostic methods.

I claim:

1. Method for production of ceramic implant material, preferably ceramic implant material including hydroxyl apatite, characterized by using for the production the spongy parts of joints from animals, preferably grown-up cattle, removing the organic constituents of the spongy parts of the joints by a quick burning, effecting one or more flushings of the remaining inorganic parts of the joints without chemical additives and sintering of said inorganic parts of the joints.

2. A method for producing ceramic implant material comprising hydroxyapatite, the method consisting essentially of the steps of:
   (a) obtaining a bone part from a joint of an animal;
   (b) Cooling the bone part to a temperature of about 0° C.;
   (c) heating the cooled bone part in a furnace to remove a substantial amount of organic constituents from the bone part;
   (d) washing the bone part with a non-acid bath after the heating of the bone part; and
   (e) sintering the bone part after said washing step; said heating in step (c) being performed with the infusion of excess oxygen into the furnace and without the maximum temperature exceeding the phase transformation temperature of the bone part.

3. The method of claim 2 wherein the bone part is an epiphysary or a metaphysary part.

4. The method of claim 3 wherein the heating in step (c) is performed in a short period of time and at a high temperature effective to remove organic constituents from the bone part without significantly raising the temperature at the center of the bone part.

5. The method of claim 4 in which step (b) is performed without pretreatment of the bone part between steps (a) and (b).

6. The method of claim 5 wherein the heating step of step (c) lasts from a few seconds to a maximum of thirty minutes.

7. The method of claim 6 including the further step (f) of washing the bone part following the sintering step (e) with a non-acid bath.

8. The method of claim 7 in which the pH of the ceramic implant material after the completion of step (f) is within the range of 6 to 12.

9. The method of claim 8 wherein said bath of step (d) comprises an aqueous fluid in an amount effective to dissolve solulizable components.

10. The method of claim 9 wherein the animal is a member of the cattle family.

11. The method of claim 10 wherein the animal is adult.

12. The method of claim 11 wherein the bone part is from the part of a hip joint, knee joint, shoulder joint or elbow joint of the animal.

13. The method of claim 12 wherein in step (c) the bone part is heated to above the ignition or inflammation temperature of the bone part.

14. A method for producing ceramic implant material comprising hydroxyapatite, the method consisting essentially of the steps of
   (a) obtaining a bone part from a joint of an animal;
   (b) cooling the bone part to a temperature of about −18° C.;
   (c) heating the cooled bone part in a furnace for about ten minutes at about 650° C. to remove a substantial amount of organic constituents from the bone part;
   (d) washing the bone part with a non-acid bath after the heating of the bone part;
   (e) sintering the bone part after said washing step of step (d); and
   (f) washing the sintered bone part with a non-acid bath obtain a desires pH in the range of about 6 to 12;
   said heating in step (c) being performed with the infusion of excess oxygen into the furnace and without the maximum temperature exceeding the phase transformation temperature of the bone part.

15. The method of claim 14 wherein the bone part is an epiphysary or a metaphysary part.

16. The method of claim 15 wherein the heating in step (c) is performed in a short period of time and at a high temperature effective to remove organic constituents from the bone part without significantly raising the temperature at the center of the bone part.

17. The method of claim 16 in which step (b) is performed without pretreatment of the bone part between steps (a) and (b).

18. The method of claim 17 wherein the heating step of step (c) lasts from a few seconds to a maximum of thirty minutes.

19. The method of claim 18 wherein said bath of step (d) comprises an aqueous fluid in an amount effective to dissolve solulizable components.

20. The method of claim 19 wherein the animal is a member of the cattle family.

21. The method of claim 20 wherein the animal is adult.

22. The method of claim 21 wherein the bone part is from the soft part of a hip joint, knee joint, shoulder joint or elbow joint of the animal.

23. The method of claim 22 wherein in step (c) the bone part is heated to above the ignition or inflammation temperature of the part.

24. A method for producing ceramic implant material comprising hydroxyapatite, comprising the steps of
   (a) obtaining a bone part from a joint of an animal;
   (b) cooling said bone part to a cold temperature;
   (c) heating said bone part in a furnace for a short time and at a high temperature effective to remove organic constituents from said bone part;
   (d) washing said bone part with a fluid free of chemical
   (e) sintering said bone part; and
   (f) washing said bone part following the sintering of step (e) with a fluid comprising metallic salt solutions for protection against bacteria;
   said heating in step (c) being performed With the infusion of excess oxygen into the furnace and without the maximum temperature exceeding the phase transformation temperature of the bone part.

25. The method of claim 24 wherein metals from said metallic salt solutions are bonded to said bone part.

* * * * *